(12) United States Patent
Kato

(10) Patent No.: US 12,212,375 B2
(45) Date of Patent: Jan. 28, 2025

(54) PROCESSING APPARATUS, COMPUTER-READABLE RECORDING MEDIUM, AND OPERATION METHOD

(71) Applicant: OLYMPUS CORPORATION, Tokyo (JP)

(72) Inventor: Yukako Kato, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 336 days.

(21) Appl. No.: 17/898,852

(22) Filed: Aug. 30, 2022

(65) Prior Publication Data

US 2022/0416917 A1    Dec. 29, 2022

Related U.S. Application Data

(63) Continuation of application No. PCT/JP2020/009787, filed on Mar. 6, 2020.

(51) Int. Cl.
*H04B 17/309* (2015.01)
*A61B 1/04* (2006.01)

(52) U.S. Cl.
CPC ........... *H04B 17/309* (2015.01); *A61B 1/041* (2013.01)

(58) Field of Classification Search
CPC ... H04B 17/309; A61B 1/041; A61B 1/00016; A61B 5/073
See application file for complete search history.

(56) References Cited

U.S. PATENT DOCUMENTS

| 8,255,046 B2* | 8/2012 | Sarkar | A61N 1/36521 600/509 |
| 9,806,777 B1* | 10/2017 | Doostnejad | H04B 7/0617 |
| 2007/0002038 A1 | 1/2007 | Suzuki et al. | |
| 2007/0182634 A1* | 8/2007 | Yamamoto | H01Q 3/28 343/700 MS |

(Continued)

FOREIGN PATENT DOCUMENTS

| JP | 2005-296112 A | 10/2005 |
| JP | 2006-305322 A | 11/2006 |

(Continued)

OTHER PUBLICATIONS

International Search Report dated May 12, 2020 received in PCT/JP2020/009787.

*Primary Examiner* — Dominic E Rego
(74) *Attorney, Agent, or Firm* — Scully, Scott, Murphy & Presser, P.C.

(57) ABSTRACT

A processing apparatus includes a processor configured to: compare a first index with a first reference value that has been determined for the first index, the first index indicating a receiving performance of a wireless signal that has been received by a receiving antenna from a medical device; perform switching to a first mode or a second mode based on a result of the comparing; and when the switching has been performed to the second mode, set a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

19 Claims, 12 Drawing Sheets

(56) References Cited

U.S. PATENT DOCUMENTS

| | | | |
|---|---|---|---|
| 2009/0160638 A1* | 6/2009 | Jesme | H01Q 1/2216 |
| | | | 340/539.11 |
| 2010/0280340 A1 | 11/2010 | Homan et al. | |
| 2013/0023217 A1* | 1/2013 | Zhuang | H04W 24/02 |
| | | | 455/63.1 |
| 2015/0119658 A1* | 4/2015 | Osorio | A61B 5/7275 |
| | | | 600/301 |
| 2017/0127353 A1* | 5/2017 | Meacci | H04W 52/0229 |
| 2017/0358851 A1* | 12/2017 | Diamond | H01Q 3/08 |
| 2020/0133167 A1* | 4/2020 | Sunahara | G03G 15/55 |
| 2022/0416917 A1* | 12/2022 | Kato | H04B 17/309 |
| 2023/0372614 A1* | 11/2023 | Osorio | G16H 50/70 |

FOREIGN PATENT DOCUMENTS

| | | |
|---|---|---|
| JP | 2008-200191 A | 9/2008 |
| WO | 2010/044389 A1 | 4/2010 |

* cited by examiner

PROCESSING APPARATUS, COMPUTER-READABLE RECORDING MEDIUM, AND OPERATION METHOD

CROSS-REFERENCE TO RELATED APPLICATION

This application is a continuation of International Application. No. PCT/JP2020/009787, filed on Mar. 6, 2020, the entire contents of which are incorporated herein by reference.

BACKGROUND

1. Technical Field

The present disclosure relates to a processing apparatus, a computer-readable recording medium, and an operation method.

2. Related Art

In the related art, as a medical observation device that is introduced into a body of a subject such as a patient and observes an inside of the subject, an endoscope has widely spread. In addition, in recent years, a capsule endoscope serving as a swallow-type image obtaining apparatus that includes, in a capsule-shaped casing, an imaging device, a communication device that wirelessly transmits image data captured by this imaging device to an outside of a body, or the like has been developed (for example, see JP 2008-200191 A). The capsule endoscope is swallowed from the mouth of a patient in order to observe an inside of a subject, then moves inside an organ, such as the esophagus, the stomach, or the small intestine, according to peristalsis, and sequentially captures an image, while the capsule endoscope is spontaneously discharged from the subject.

During a movement inside the subject, image data captured by the capsule endoscope is sequentially transmitted to the outside of the body by using wireless communication, and the image data is stored via a receiving antenna in a memory that is provided inside or outside a receiving device outside the body, or an image is displayed on a display that is provided in the receiving device. A doctor or a nurse can take the image data stored in the memory into an information processing apparatus via a cradle into which the receiving device has been inserted, and can make a diagnosis on the basis of an image that is displayed on a display of this information processing apparatus.

A plurality of receiving antennas that each receives a wireless signal transmitted by the capsule endoscope is mounted on the subject. Each of the plurality of receiving antennas is attached according to a route of the capsule endoscope that moves inside the subject.

SUMMARY

In some embodiments, a processing apparatus includes a processor configured to: compare a first index with a first reference value that has been determined for the first index, the first indicating a receiving performance of a wireless signal that has been received by a receiving antenna from a medical device configured to capture an image of an inside of a subject; perform switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and when the switching has been performed to the second mode, set a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

In some embodiments, provided is a non-transitory computer-readable recording medium with an executable program stored thereon. The program causes a processing apparatus to execute: comparing a first index with a first reference value that has been determined for the first index, the first index indicating a receiving performance of a wireless signal that has been received by a receiving antenna from a medical device configured to capture an image of an inside of a subject; performing switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and when the switching has been performed to the second mode, setting a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

In some embodiments, an operation method includes: comparing a first index with a first reference value that has been determined for the first index, the first index indicating a receiving performance of a wireless signal that has been received by a receiving antenna from a medical device configured to capture an image of an inside of a subject; performing switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and when the switching has been performed to the second mode, setting a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

The above and other features, advantages and technical and industrial significance of this disclosure will be better understood by reading the following detailed description of presently preferred embodiments of the disclosure, when considered in connection with the accompanying drawings.

DETAILED DESCRIPTION

As an embodiment according to the disclosure, a capsule endoscope system that uses a medical capsule endoscope is described below. Note that in the description of the drawings, the same portion is denoted by the same reference sign. In addition, the drawings are schematic, and it needs to be noted that a relationship between a thickness and a width of each member, a ratio of respective members, or the like is different from an actual one.

First Embodiment

Figure 1:
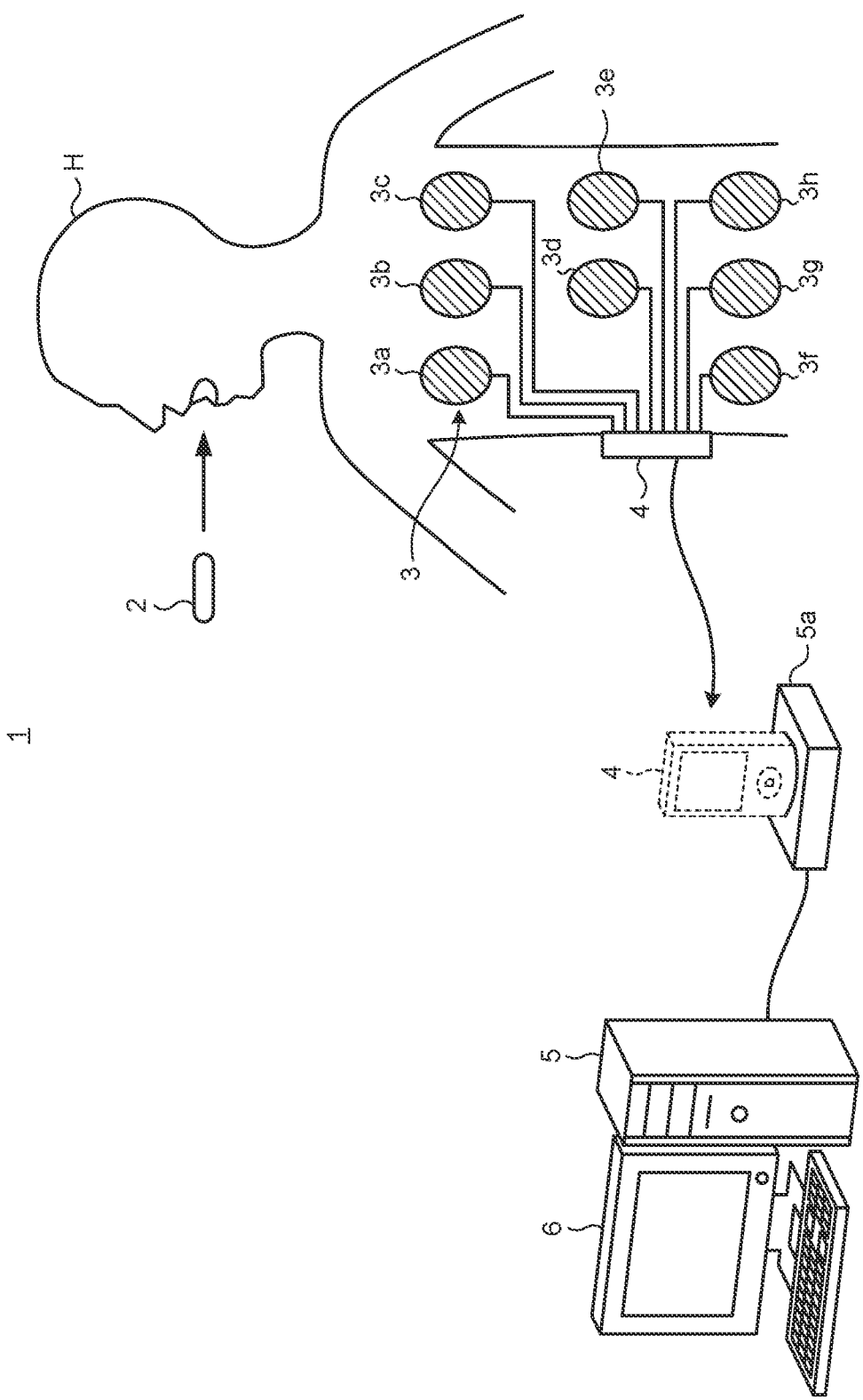
FIG. 1 is a schematic diagram illustrating a schematic configuration of a capsule endoscope system according to a first embodiment of the disclosure.

FIG. 1 is a schematic diagram illustrating a schematic configuration of a capsule endoscope system according to a first embodiment of the disclosure. A capsule endoscope system 1 illustrated in FIG. 1 includes: a capsule endoscope 2 that is introduced into a subject H, captures an image of an inside of the subject H to generate image data, superimposes the image data onto a wireless signal, and transmits the wireless signal on radio waves; a receiving device 4 that receives the wireless signal transmitted from the capsule endoscope 2, via a receiving antenna unit 3 that includes a plurality of receiving antennas (receiving antennas 3*a* to 3*h*) that is mounted on the subject H; and a processing apparatus 5 that takes in an image signal captured by the capsule endoscope 2 from the receiving device 4 via a cradle 5*a*, processes the image data, and generates image data indicating an image inside the subject H. The image data generated by the processing apparatus 5 is displayed and output, for example, in a display device 6. The plurality of receiving antennas and the receiving device 4 configure a receiving system.

Figure 2:
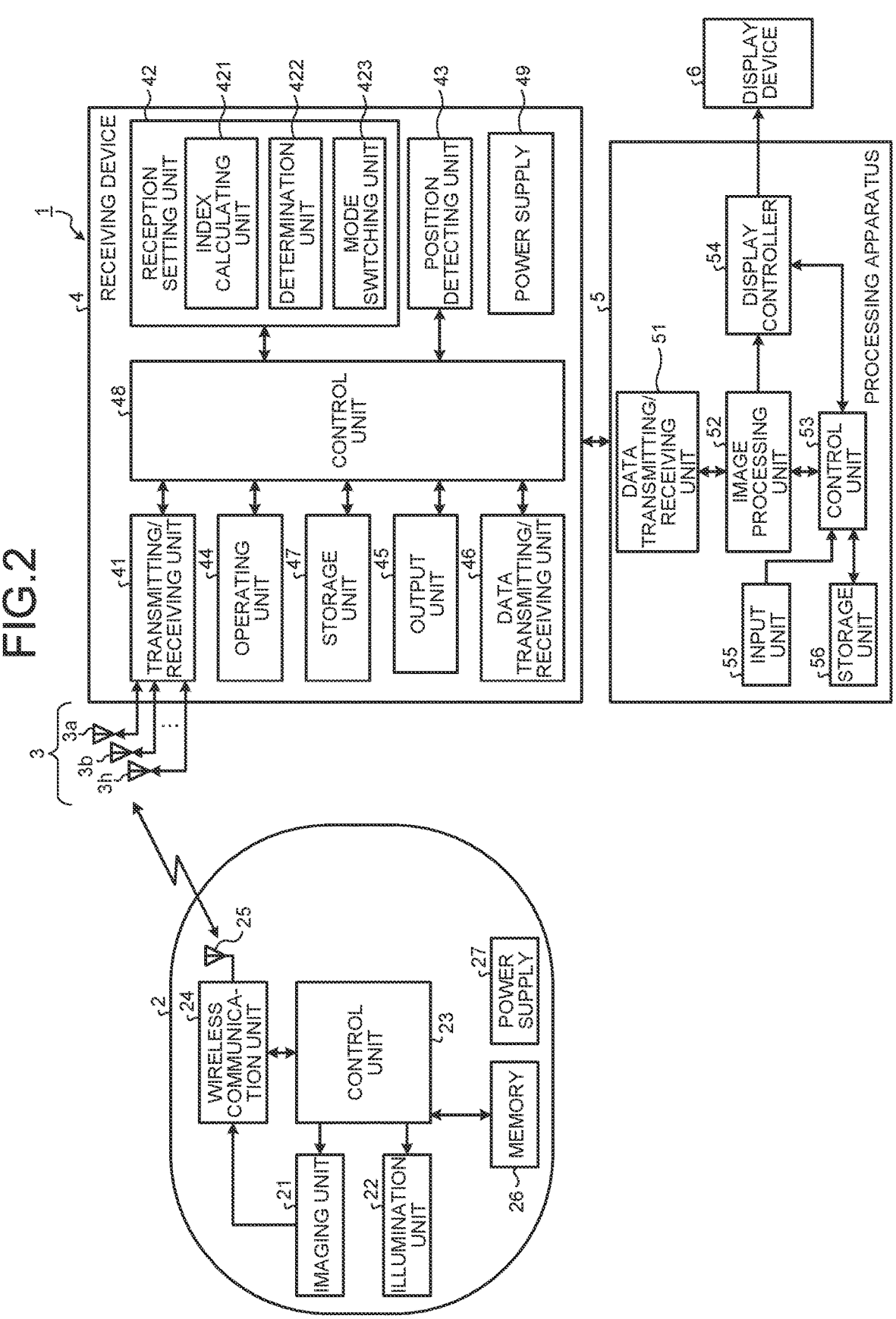
FIG. 2 is a block diagram illustrating a schematic configuration of the capsule endoscope system according to the first embodiment of the disclosure.

FIG. 2 is a block diagram illustrating a schematic configuration of the capsule endoscope system according to the first embodiment of the disclosure. The capsule endoscope 2 includes an imaging unit 21, an illumination unit 22, a control unit 23, a wireless communication unit 24, a memory 26, and a power supply 27. The capsule endoscope 2 is a device in which the respective components described above are incorporated into a capsule-shaped casing having a size that allows the subject H to swallow the casing.

The imaging unit 21 includes, for example, an imaging element that generates image data obtained by imaging an inside of the subject H, from an optical image formed on a light receiving surface, and outputs the image data, and an optical system, such as an objective lens, that is disposed on a side of the light receiving surface of the imaging element. In the imaging element, a plurality of pixels that each receives light from the subject H is arranged in a matrix shape, and optical-to-electrical conversion is performed on the light received by the plurality of pixels, and therefore image data is generated. The imaging unit 21 reads a pixel value in each horizontal line of the plurality of pixels that is arranged in a matrix shape, and generates image data including plural pieces of line data in which a synchronizing signal has been added to each of the horizontal lines. The imaging unit 21 is configured by using a charge coupled device (CCD) imaging element or a complementary metal oxide semiconductor (CMOS) imaging element.

The illumination unit 22 is configured by using a white light emitting diode (LED) that generates white light serving as illumination light, or the like. Note that, rather than the white LED, a configuration that generates white light by combining rays of light of a plurality of LEDs, laser light sources, or the like that is different in an emission wavelength band may be employed, or a configuration using a xenon lamp, a halogen lamp, or the like may be employed.

The control unit 23 controls operation processing of each of the components of the capsule endoscope 2. For example, in a case where the imaging unit 21 performs imaging processing, the control unit 23 causes the imaging element to perform exposure processing and reading processing, and causes the illumination unit 22 to apply illumination light according to an exposure timing of the imaging unit 21. The control unit 23 is configured by using a general-purpose processor such as a central processing unit (CPU) or a dedicated processor of various arithmetic circuits or the like that perform a specified function, such as an application specific integrated circuit (ASIC).

The wireless communication unit 24 performs modulation processing on the image data that has been output from the imaging unit 21, and transmits the image data to an outside. The wireless communication unit 24 performs A/D conversion and predetermined signal processing on the image data that has been output from the imaging unit 21, obtains image data of a digital format, superimposes the image data together with relevant information onto a wireless signal, and transmits the wireless signal from an antenna 25 to the outside. The relevant information includes identification information (for example, a serial number) of the capsule endoscope 2 that has been assigned in order to identify an individual of the capsule endoscope 2, identification information (for example, an imaging number) of image data to be transmitted, or the like. Note that the wireless communication unit 24 may be configured to receive, from the antenna 25, a control signal that has been transmitted from the receiving device 4.

The memory 26 stores an execution program and a control program that cause the control unit 23 to perform various operations, and a parameter such as a threshold. The memory 26 is configured by using a volatile memory, a non-volatile memory, or a combination thereof. The memory 26 is configured by using a random access memory (RAM), a read only memory (ROM), or the like.

The power supply 27 includes a battery that includes a button cell or the like, a power supply circuit that supplies power to each unit, and a power supply switch that switches an ON state and an OFF state of the power supply 27, and after the power supply switch has entered into the ON state, the power supply 27 supplies power to each of the units in the capsule endoscope 2. Note that the power supply switch includes, for example, a reed switch that can switch the ON state and the OFF state by using external magnetic force, and before the use of the capsule endoscope 2 (before the subject H swallows the capsule endoscope 2), magnetic force is applied to the capsule endoscope 2 from the outside, and therefore switching is performed to the ON state.

After such a capsule endoscope 2 has been swallowed by the subject H, the capsule endoscope 2 sequentially captures an image of a biological region (the esophagus, the stomach, the small intestine, the large intestine, and the like) in a predetermined period (for example, a period of 0.5 seconds) while moving inside the gastrointestinal tract of the subject H according to peristalsis of organs, or the like. Then, an image signal that has been obtained in this imaging operation and relevant information are sequentially transmitted wirelessly to the receiving device 4.

Here, configurations of the receiving antennas 3a to 3h are described with reference to FIG. 3. Each of the receiving antennas receives a wireless signal from the capsule endoscope 2.

Figure 3:
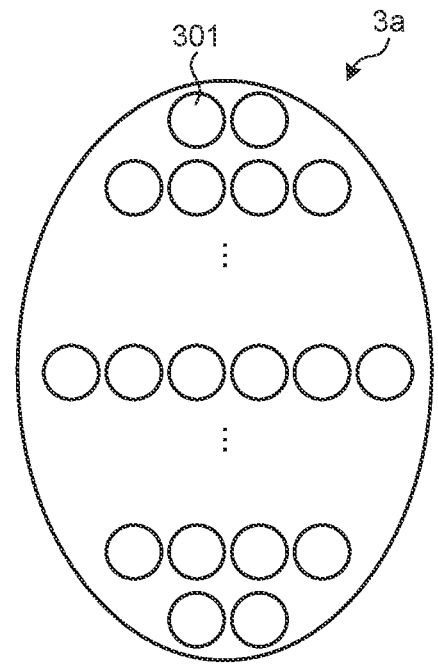
FIG. 3 is a diagram illustrating a configuration of a receiving antenna in the capsule endoscope system according to the first embodiment of the disclosure.

FIG. 3 is a diagram illustrating a configuration of the receiving antenna in the capsule endoscope system according to the first embodiment of the disclosure. The receiving antennas 3a to 3h have the same configuration. FIG. 3 illustrates an example of a configuration of the receiving antenna 3a. The receiving antenna 3a includes an antenna element 301 that can control an amplitude and a phase. In the receiving antenna 3a, a radiation direction can be changed by changing an amplitude and a phase of the antenna element 301. The radiation direction described here corresponds to a direction in which the receiving antenna 3a can receive a wireless signal. A plurality of antenna elements 301 is arranged in a matrix shape on a signal receiving surface of the receiving antenna 3a. The receiving antenna 3a receives a wireless signal by summing signals of the antenna elements 301 under the control of the receiving device 4. In the receiving antenna 3a, antenna elements 301 serving as targets for summing are changed, and therefore a radiation direction or a value of a half-power angle of the receiving antenna 3a is changed, and a signal receiving area or its receiving characteristic is changed.

Figure 4:
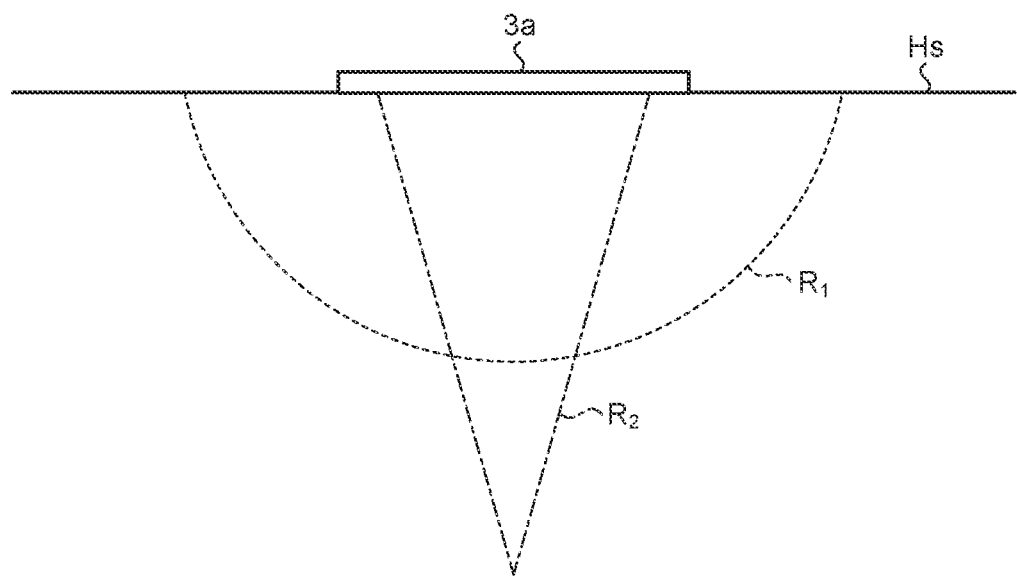
FIG. 4 is a diagram explaining a receiving area of the receiving antenna in the capsule endoscope system according to the first embodiment of the disclosure.

FIG. 4 is a diagram explaining a receiving area of the receiving antenna in the capsule endoscope system according to the first embodiment of the disclosure. For example, if a value of the half-power angle of the antenna element 301 is increased, the receiving antenna 3a receives a signal in a receiving area $R_1$. On the other hand, if a value of the half-power angle of the antenna element 301 is decreased, the receiving antenna 3a receives a signal in a receiving area $R_2$ that is smaller than the receiving area $R_1$. The receiving antenna 3a can change an orientation or a range in which a signal is received by changing a value of the half-power angle of the antenna element 301. The receiving area $R_2$ has a narrow area relative to a signal receiving surface of a receiving antenna, but has a long distance in which a wireless signal can be received, in comparison with the receiving area $R_1$. Stated another way, in a case where the receiving antenna 3a has been set to have the receiving area $R_2$, the receiving antenna 3a has a sensitivity in an area that is narrow in the radiation direction of a wireless signal of the receiving antenna 3a, but is deep from a body surface $H_S$ of the subject H, in comparison with the receiving area $R_1$.

In a narrow half-power angle mode in which the half-power angle is set to have a small value, a receiving area $R_2$ of a target receiving antenna is set. An orientation of the receiving area $R_2$ is set to an orientation in which a wireless signal in any section of plural preset scanned sections is received. In the narrow half-power angle mode, each of the scanned sections is sequentially scanned, and a scanned section is selected on the basis of the index described later. In the narrow half-power angle mode, an orientation of the receiving area $R_2$ toward a scanned section to be set is set, and a wireless signal in the scanned section is received by the receiving antenna.

Figure 5:
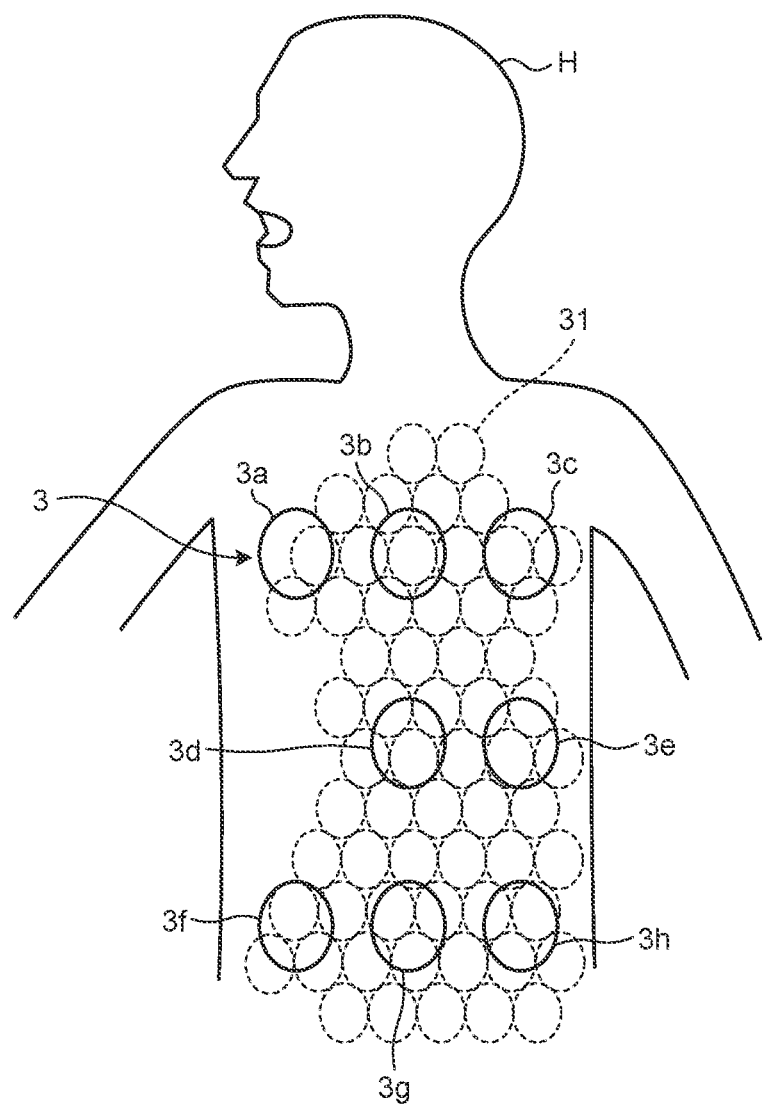
FIG. 5 is a diagram explaining a scanned section of the receiving antenna in the capsule endoscope system according to the first embodiment of the disclosure.

FIG. 5 is a diagram explaining a scanned section of a receiving antenna in the capsule endoscope system according to the first embodiment of the disclosure. A scanned section 31 is an area that is set for the subject H. In the present first embodiment, a plurality of scanned sections 31 as set for an area that the capsule endoscope 2 can pass through. The plurality of scanned sections 31 is set, for example, in positions where the presence of the gastrointestinal tract is expected. A scanned section to be allocated to each of the receiving antennas may be set by a user by using an operating unit 44, or may be automatically set by the receiving device 4 on the basis of a position of each of the receiving antennas. In a case where the receiving device 4 automatically allocates a scanned section, the receiving device 4 allocates a scanned section to a receiving antenna on the basis of conditions such as a distance from the receiving antenna to the scanned section or the number of scanned sections to be allocated.

A user mounts the receiving antennas 3a to 3h on the subject H, and then sets mounting positions of the receiving antennas 3a to 3h relative to the subject H, on an image of the subject H displayed on the display device 6, by using, for example, the operating unit 44 described later. After this setting, a scanned section of each of the receiving antennas is manually or automatically allocated. Then, in the narrow half-power angle mode, under the control of the receiving device 4, a scanning order is set for the scanned section that has been allocated to each of the receiving antennas in accordance with preset conditions. The scanning order is an order of a section toward which a radiation direction is set in a receiving antenna.

Return to FIG. 2. The receiving device 4 includes a transmitting/receiving unit 41, a reception setting unit 42, a position detecting unit 43, an operating unit 44, an output unit 45, a data transmitting/receiving unit 46, a storage unit 47, a control unit 48, and a power supply 49.

The transmitting/receiving unit 41 receives a wireless signal that the capsule endoscope 2 has wirelessly transmitted via the receiving antenna unit 3, or transmits a control signal that changes receiving modes of the receiving antennas 3a to 3h. The transmitting/receiving unit 41 receives, via the receiving antennas 3a to 3h, image data and relevant information that have been wirelessly transmitted from the capsule endoscope 2. The transmitting/receiving unit 41 demodulates the received signal, and outputs the demodulated signal to the data transmitting/receiving unit 46 or the storage unit 47. The transmitting/receiving unit 41 is configured by using a transmitter/receiver.

The reception setting unit 42 sets a receiving area or the like of a signal received by the receiving antennas 3a to 3h. The reception setting unit 42 includes an index calculating unit 421, a determination unit 422 and a mode switching unit 423. The reception setting unit 42 is configured by using a general-purpose processor such as a CPU, or a dedicated processor of various arithmetic circuits or the like that perform a specified function, such as an ASIC.

The index calculating unit 421 calculates an index on the basis of a signal of each of the receiving antennas. As the index, a value indicating receiving performance of a wireless signal is used, and examples include a received signal strength indicator (RSSI), a counted value of a sync word, and a counted value of a bit error. In the present first embodiment, an example where the RSSI is used as the index is described.

The determination unit 422 compares the index calculated by the index calculating unit 421 with a preset reference value, and determines a magnitude relationship. For example, in a case where the index is the RSSI or a counted value of the sync word, the determination unit 422 determines whether the index exceeds the reference value. For example, the determination unit 422 determines whether each of the indices of the receiving antennas 3a to 3h exceeds the reference value. In contrast, in a case where the index is a counted value of the bit error, the determination unit 422 determines whether the index is below the reference value.

The mode switching unit 423 switches signal receiving modes of the receiving antennas 3a to 3h on the basis of a result of determination performed by the determination unit 422. The mode switching unit 423 performs switching to any of a wide area mode in which a half-power angle is set to have a great value and a signal as received in the receiving area $R_1$, and a narrow half-power angle mode in which a half-power angle is set to have a small value and a signal is received in the receiving area $R_2$, on the basis of a result of determination performed by the determination unit 422.

The position detecting unit 43 performs an arithmetic operation to detect a position of the capsule endoscope 2 by using respective pieces of received signal strength indicator information of the receiving antennas 3a to 3h that have been input from the transmitting/receiving unit 41. The position detecting unit 43 outputs a result of detecting the position of the capsule endoscope 2 as positional information of the capsule endoscope 2 to the control unit 48, and stores the result in the storage unit 47. In addition, the position detecting unit 43 may detect the position of the capsule endoscope 2 by using a publicly known method, for example, JP 2007-283001 A, or may detect the position of the capsule endoscope 2 by using a magnetic field for position detection. The position detecting unit 43 is configured by using a CPU, an ASIC, or the like.

The operating unit 44 is an input device that is used for a user to input various types of setting information or instruction information to the receiving device 4. The operating unit 44 is configured by using, for example, a switch, a button, or the like that is provided in an operating panel of the receiving device 4.

The output unit 45 displays an image, outputs sound or light, or generates vibration. The output unit 45 is configured by using at least one of a display such as a liquid crystal display or an organic EL display, a speaker, a light source, and a vibration generator such as a vibration motor.

The data transmitting/receiving unit 46 transmits, to the processing apparatus 5, image data and relevant information that have been stored in the storage unit 47, when the data transmitting/receiving unit 46 is connected to the processing apparatus 5 in a communicable state. The data transmitting/receiving unit 46 is configured by using a communication interface such as a USB or a LAN.

The storage unit 47 stores a program for causing the receiving device 4 to operate and perform various functions, image data obtained by the capsule endoscope 2, a reference value for determination processing, or the like. The storage unit 47 is configured by using a RAM, a ROM, or the like.

The control unit 48 controls each constituent unit of the receiving device 4. The control unit 48 controls a receiving mode of a signal from the capsule endoscope 2, for example, in accordance with a mode switched by the mode switching unit 423. The control unit 48 is configured by using a general-purpose processor such as a CPU, or a dedicated processor of various arithmetic circuits or the like that perform a specified function, such as an ASIC.

The power supply 49 supplies power to each unit of the receiving device 4. The power supply 49 is configured by using a battery including a cell or the like.

Such a receiving device 4 is mounted on the subject H and is carried while the capsule endoscope 2 is performing imaging, for example, after the capsule endoscope 2 is swallowed by the subject H and before the capsule endoscope 2 passes through the gastrointestinal tract, and is discharged. During this period, the receiving device 4 stores, in the storage unit 47, image data that has been received via the receiving antenna unit 3.

After the capsule endoscope 2 has finished imaging, the receiving device 4 is removed from the subject H, and is set in the cradle 5a (see FIG. 1) that is connected to the processing apparatus 5. By doing this, the receiving device 4 is connected to the processing apparatus 5 in a communicable state, and transfers (downloads) image data and relevant information that have been stored in the storage unit 47 to (into) the processing apparatus 5.

The processing apparatus 5 is configured by using, for example, a work station including the display device 6 such as a liquid crystal display. The processing apparatus 5 includes a data transmitting/receiving unit 51, an image processing unit 52, a control unit 53, a display controller 54, an input unit 55, and a storage unit 56.

The data transmitting/receiving unit 51 is connected to the receiving device 4 via the cradle 5a, and transmits/receives data to/from the receiving device 4. The data transmitting/receiving unit 51 is configured by using a communication interface such as a USB or a LAN.

The image processing unit 52 reads a predetermined program stored in the storage unit 56 described later, and therefore the image processing unit 52 performs predetermined image processing for generating an image that corresponds to image data that has been input from the data transmitting/receiving unit 51, or image data that has been stored in the storage unit 56. The image processing unit 52 is implemented by a general-purpose processor such as a CPU, or a dedicated processor of various arithmetic circuits or the like that perform a specified function, such as an ASIC.

The control unit 53 reads various programs stored in the storage unit 56, and therefore the control unit 53 provides an instruction to each unit that configures the processing apparatus 5, transfers data, or performs another operation on the basis of a signal that has been input from the input unit 55 or image data that has been input from the data transmitting/receiving unit 51, and integrally controls an operation of the entirety of the processing apparatus 5. The control unit 53 is implemented by a general-purpose processor such as a CPU, or a dedicated processor of various arithmetic circuits or the like that perform a specified function, such as an ASIC.

The display controller 54 performs predetermined processing, such as data thinning according to a display range of an image in the display device 6 or grayscale processing, on an image generated by the image processing unit 52, and causes the display device 6 to display and output an obtained image together with information relating to a display target such as a final score. The display controller 54 is implemented, for example, by a general-purpose processor such as a CPU, or a dedicated processor of various arithmetic circuits or the like that perform a specified function, such as an ASIC.

The input unit 55 receives an input of information or a command that corresponds to an operation performed by a user. The input unit 55 is implemented by an input device such as a keyboard, a mouse, a touch panel, or various switches.

The storage unit 56 stores a program for causing the processing apparatus 5 to operate and perform various functions, various types of information that are used during execution of the program, image data and relevant information that have been obtained from the receiving device 4, an endoscopic image generated by the image processing unit 52, and the like. The storage unit 56 is implemented by a semiconductor memory such as a flash memory, a RAM, or a ROM, a recording medium such as an HDD, an MO, a CD-R, or a DVD-R, a driving device that drives the recording medium, and the like.

Figure 6:
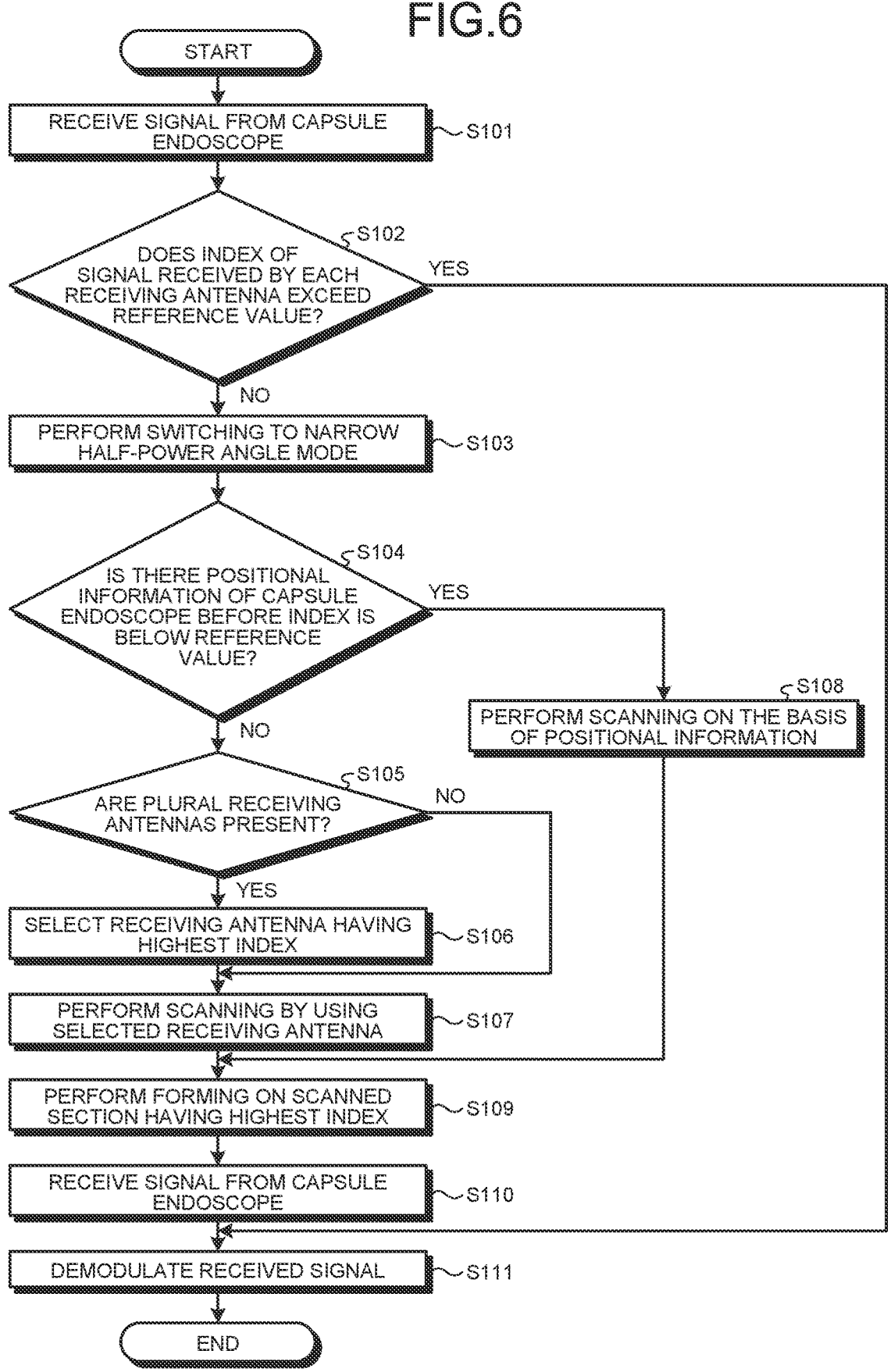
FIG. 6 is a flowchart illustrating mode switching processing at the time of obtaining image data that is performed by the capsule endoscope system according to the first embodiment of the disclosure.

Next, mode switching processing relating to obtainment of a wireless signal that is performed by the capsule endoscope system 1 is described. FIG. 6 is a flowchart illustrating mode switching processing at the time of obtaining image data that is performed by the capsule endoscope system according to the first embodiment of the disclosure. Note that description is provided under the assumption that the wide area mode is set at the time of driving a device.

First, in Step S101, each of the receiving antennas 3a to 3h receives a wireless signal from the capsule endoscope 2. At this time, the index calculating unit 421 calculates an index by using the wireless signal obtained via the transmitting/receiving unit 41. In Step S101, the index calculating unit 421 calculates an RSSI for each of the receiving antennas.

In Step S102, the determination unit 422 determines whether the calculated index exceeds a reference value. In the present first embodiment, in a case where the determination unit 422 has determined that at least one RSSI exceeds the reference value (Step S102: Yes), the control unit 48 selects a receiving antenna having a greatest RSSI, and the processing moves on to Step S111. In contrast, in a case where the determination unit 422 has determines that all of the RSSIs are below the reference value (Step S102: No), the processing of the determination unit 422 moves on to Step S103.

In Step S103, the mode switching unit 423 performs switching from the wide area mode to the narrow half-power angle mode.

In Step S104, the control unit 48 determines whether there is positional information of the capsule endoscope 2 before the index is below the reference value, in the narrow half-power angle mode. The control unit 48 determines whether there is a receiving antenna having a previous index that exceeds the reference value, and therefore the control unit 48 determines whether there is positional information of the capsule endoscope 2 before the index is below the reference value. In a case where the control unit 48 has determined that there is no positional information of the capsule endoscope 2 before the index is below the reference value (Step S104: No), the processing moves on to Step S105. In contrast, in a case where the control unit 48 has determined that there is positional information of the capsule endoscope 2 before the index is below the reference value (Step S104: Yes), the processing moves on to Step S108. At this time, the control unit 48 extracts a receiving antenna having a previous index that exceeds the reference value. The control unit 48 refers to the storage unit 47, and obtains positional information of the capsule endoscope 2 at the time when the extracted receiving antenna has obtained the signal.

In Step S105, the control unit 48 determines whether a plurality of receiving antennas is mounted to the subject H. In a case where the control unit 48 has determined that a plurality of receiving antennas is mounted on the subject H (Step S105: Yes), the processing moves on to Step S106. In contrast, in a case where the control unit 48 has determined that a single receiving antenna is mounted on the subject H (Step S105: No), the control unit 48 selects the receiving antenna, and the processing moves on to Step S107.

In Step S106, the control unit 48 selects a receiving antenna having a highest index.

In Step S107, the control unit 48 causes the receiving antenna selected in Step S105 or S106 to perform scanning. The receiving antenna receives a signal from the capsule endoscope 2 in an order that has been set for allocated scanned sections. The index calculating unit 421 calculates an RSSI for each of the scanned sections. After scanning has finished, the processing of the mode switching unit 423 moves on to Step S109.

In addition, in Step S108, the control unit 48 causes the receiving antenna extracted in Step S104 to perform scanning. The receiving antenna receives a signal from the capsule endoscope 2 in an order that has been set for allocated scanned sections. The index calculating unit 421 calculates an RSSI for each of the scanned sections. After scanning has finished, the processing of the control unit 48 moves on to Step S109.

In Step S109, the control unit 48 selects a scanned section having a highest index, and sets the receiving area $R_2$ in the scanned section, and therefore the control unit 48 performs forming.

In Step S110, the transmitting/receiving unit 41 receives a signal of the scanned section (the receiving area $R_2$) on which forming has been performed in Step S109.

In Step S111, the transmitting/receiving unit 41 demodulates a signal that has been received by the receiving antenna selected in Step S102, or the signal received in Step S110.

By performing the processing described above, a signal in which an index (here, an RSSI) has been satisfactorily secured can be received. After demodulating the signal, the signal is transmitted to the processing apparatus 5, and the processing described above is performed. In addition, whether the mode switching processing will need to be performed is determined, for example in frame units. For example, the mode switching processing may be performed on every several frames, or may be performed on every single frame. In a case where the mode switching processing is performed again, in Step S102, if all of the indices exceed a reference value (Step S102: Yes), the mode switching unit 423 switches a mode to the wide area mode. Note that in the flowchart described above, an example where a highest index is selected has been described. However, a receiving antenna or a scanned section is not necessarily selected on the basis of a highest index, for example, such that a second highest index may be selected, and conditions selected by a user may be set.

In the first embodiment described above, switching is performed to the wide area mode or the narrow half-power angle mode on the basis of an index that has been calculated on the basis of a received signal, and a signal of an appropriate receiving antenna or a signal of a scanned section is received. According to the present first embodiment, a wireless signal can be reliably obtained.

Second Embodiment

Figure 7:
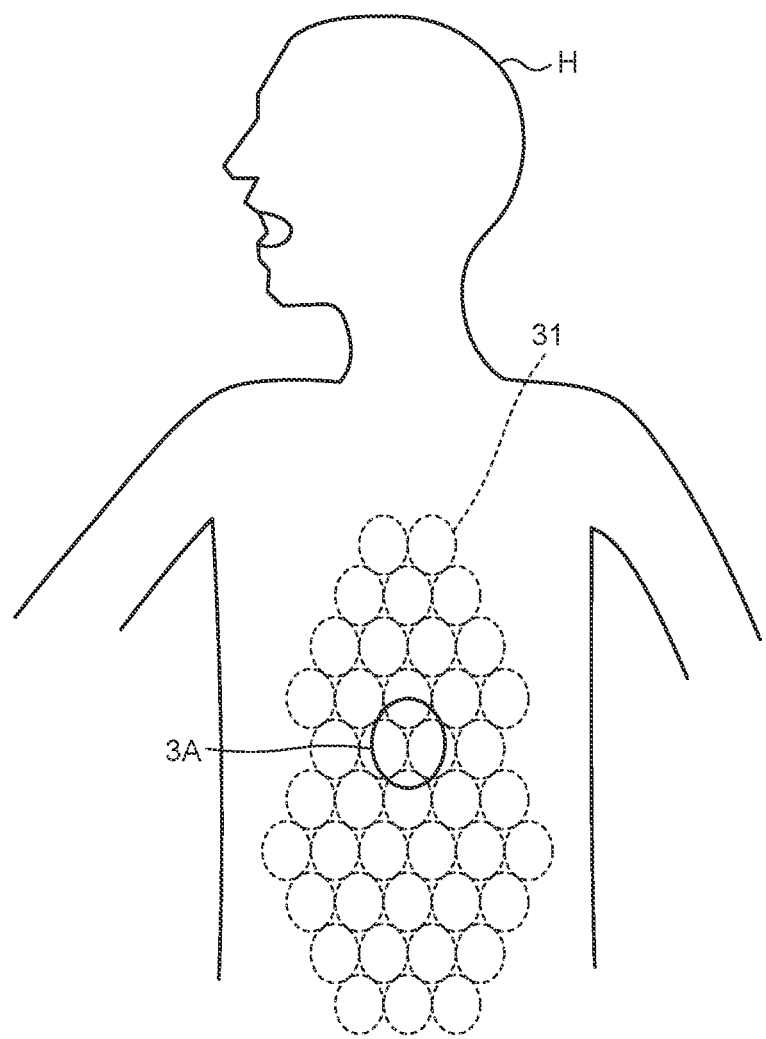
FIG. 7 is a diagram explaining a scanned section of a receiving antenna in a capsule endoscope system according to a second embodiment of the disclosure.

Next, a second embodiment of the disclosure is described. FIG. 7 is a diagram explaining a scanned section of a receiving antenna in a capsule endoscope system according to the second embodiment of the disclosure. The capsule endoscope system according to the present second embodiment includes a receiving antenna 3A instead of the receiving antenna unit 3 of the capsule endoscope system 1 according to the first embodiment. The other configurations are similar to configurations of the first embodiment. The second embodiment is different from the first embodiment in which a plurality of receiving antennas is included in that only a single receiving antenna is included. The content that is different from the content of the first embodiment is described below with reference to FIG. 7.

The receiving antenna 3A is configured by using, for example, a chip antenna or the like. In the receiving antenna 3A, in the wide area mode, the receiving area $R_1$ described above includes all of the scanned sections 31. In addition, in the narrow half-power angle mode, the receiving antenna 3A can perform forming on each of the scanned sections 31.

A user mounts the receiving antenna 3A on the subject H, and then sets a mounting position of the receiving antenna 3A relative to the subject H by using the operating unit 44 described later. By performing this setting, a scanned section (a scanning position) of the receiving antenna 3A is set. Note that a scanning order has been set in advance for the scanned section.

Mode switching processing according to the present second embodiment can be performed similarly to the flowchart of FIG. 6 described above. At this time, a single receiving antenna 3A is used, and therefore Steps S105 and S106 are not performed.

In the second embodiment described above, switching is performed to the wide area mode or the narrow half-power angle mode on the basis of an index that has been calculated on the basis of a received signal, and in the wide area mode, a signal received by the receiving antenna 3A or a signal of a scanned section is received. According to the present second embodiment, a wireless signal can be reliably obtained.

Third Embodiment

Figure 8:
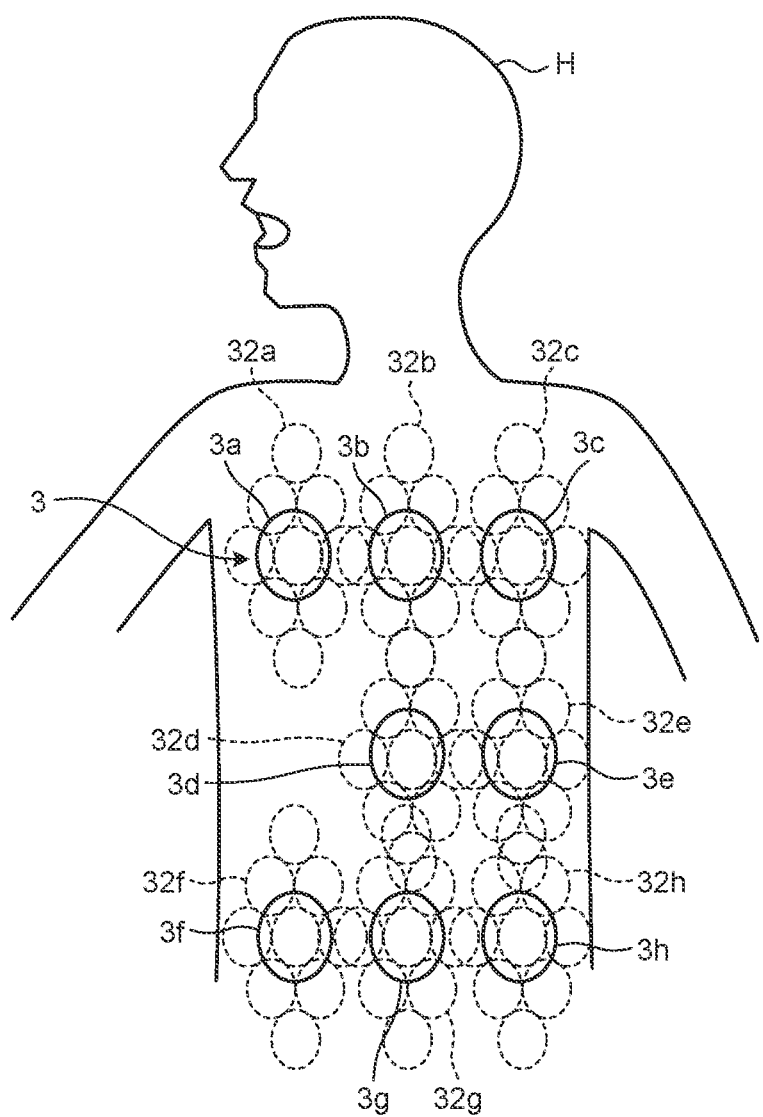
FIG. 8 is a diagram explaining a scanned section of a receiving antenna in a capsule endoscope system according to a third embodiment of the disclosure.

Next, a third embodiment of the disclosure is described. FIG. 8 is a diagram explaining a scanned section of a receiving antenna in a capsule endoscope system according to the third embodiment of the disclosure. A configuration of the capsule endoscope system according to the present third embodiment is similar to a configuration of the capsule endoscope system 1 according to the first embodiment. The third embodiment is different from the first embodiment in a scanned section that is set for each receiving antenna. The content that is different from the content of the first embodiment is described below with reference to FIG. 8.

A scanned section in which scanning will be performed is set for the receiving antennas 3a to 3h themselves. In the first embodiment described above, the scanned section 31 is set for the subject H, but in the third embodiment, a scanned section is set for the receiving antennas 3a to 3h. Specifically, a plurality of scanned sections 32a is set for the receiving antenna 3a. Similarly, a plurality of scanned sections 32b is set for the receiving antenna 3b, a plurality of scanned sections 32c is set for the receiving antenna 3c, a plurality of scanned sections 32d is set for the receiving antenna 3d, a plurality of scanned sections 32e is set for the receiving antenna 3e, a plurality of scanned sections 32f is set for the receiving antenna 3f, and a plurality of scanned sections 32h is set for the receiving antenna 3h.

Mode switching processing according to the present third embodiment can be performed similarly to the flowchart of FIG. 6 described above.

In the third embodiment described above, switching is performed to the wide area mode to the narrow half-power angle mode on the basis of an index that has been calculated on the basis of a received signal, and a signal of an appropriate receiving antenna or a signal of a scanned section is received. According to the present third embodiment, a wireless signal can be reliably obtained.

In addition, in the first embodiment described above, a user sets a mounting position of the receiving antenna unit 3 relative to the subject H, and scanned sections of the receiving antennas 3a to 3h are allocated according to this setting. In contrast, in the present third embodiment, scanned sections have been determines for each of the receiving antennas. Therefore, a user does not need to set mounting positions of the receiving antennas, and a burden imposed on the user in processing using the capsule endoscope system can be reduced.

Fourth Embodiment

Figure 9:
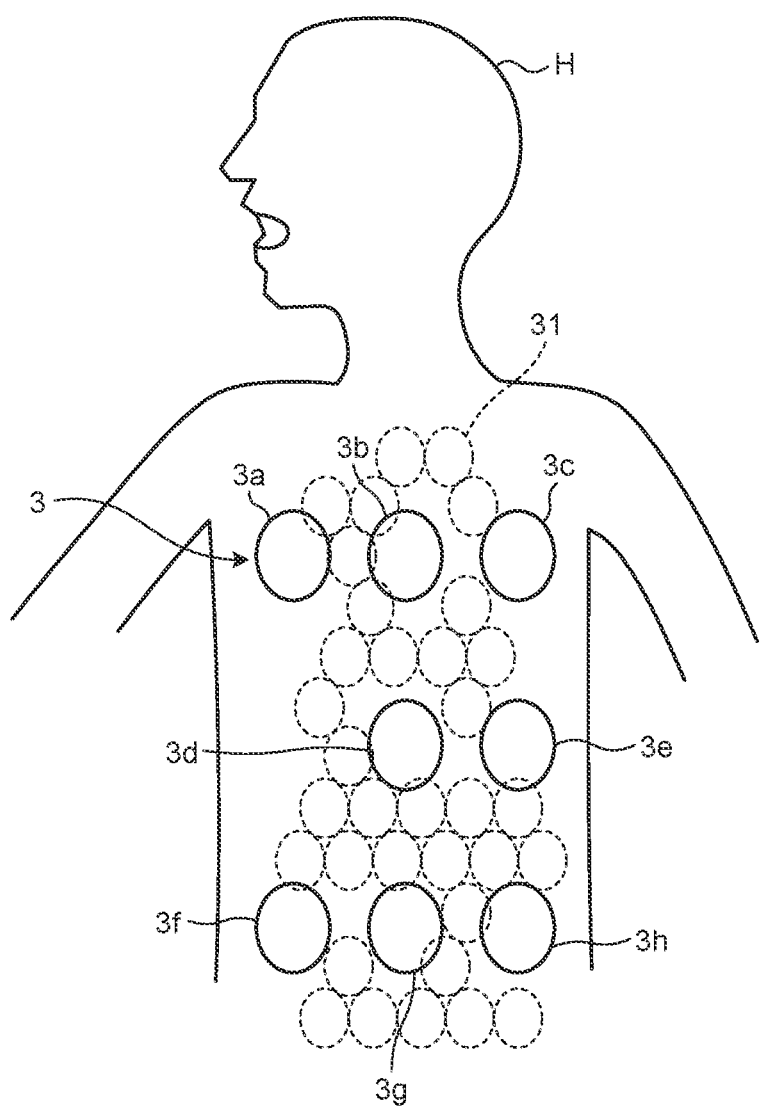
FIG. 9 is a diagram explaining a scanned section of a receiving antenna in a capsule endoscope system according to a fourth embodiment of the disclosure.

Next, a fourth embodiment of the disclosure is described. FIG. 9 is a diagram explaining a scanned section of a receiving antenna in a capsule endoscope system according to the fourth embodiment of the disclosure. A configuration of the capsule endoscope system according to the present fourth embodiment is similar to the configuration of the capsule endoscope system 1 according to the first embodiment. The fourth embodiment is different from the first embodiment in a scanned section that is set for each receiving antenna. The content that is different from the content of the first embodiment is described below with reference to FIG. 9.

A scanned section in which scanning will be performed is set for the receiving antennas 3a to 3h themselves. In the first embodiment described above, all of the scanned sections 31 that are set for the subject H are allocated to any of the receiving antennas 3a to 3h. In contrast, in the present fourth embodiment, on a body surface of the subject H, only scanned sections 31 that do not overlap the receiving antennas 3a to 3h are set as scanned sections.

Mode switching processing according to the present fourth embodiment can be performed similarly to the flowchart of FIG. 6 described above. In scanning processing according to the present fourth embodiment, the number of sections to be scanned is smaller than the number of sections to be scanned in the first embodiment described above.

In the fourth embodiment described above, switching is performed to the wide area mode or the narrow half-power angle mode on the basis of an index that has been calculated on the basis of a received signal, and a signal of an appropriate receiving antenna or a signal of a scanned section is received. According to the present fourth embodiment, a wireless signal can be reliably obtained.

In addition, in the present fourth embodiment, scanned sections are thinned and set, and therefore the time required in scanning processing can be reduced.

Fifth Embodiment

Figure 10:
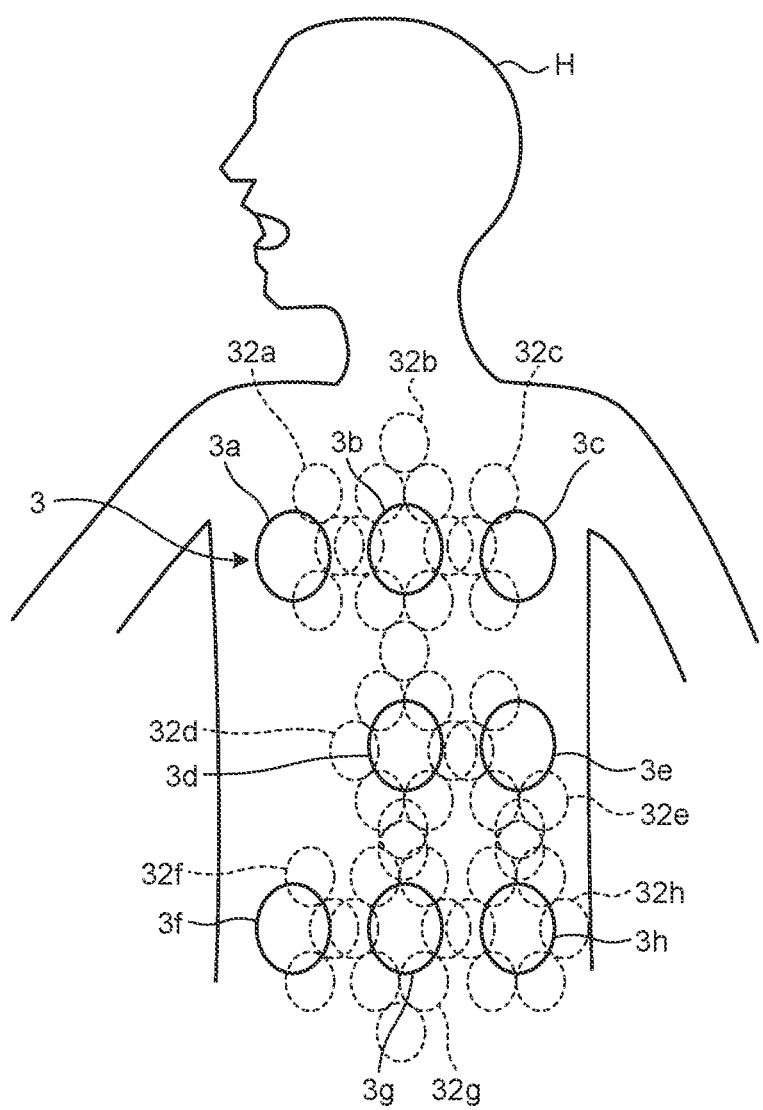
FIG. 10 is a diagram explaining a scanned section of a receiving antenna in a capsule endoscope system according to a fifth embodiment of the disclosure.

Next, a fifth embodiment of the disclosure is described. FIG. 10 is a diagram explaining a scanned section of a receiving antenna in a capsule endoscope system according to the fifth embodiment of the disclosure. A configuration of the capsule endoscope system according to the present fifth embodiment is similar to the configuration of the capsule endoscope system 1 according to the first embodiment. The fifth embodiment is different from the first embodiment in a scanned section that is set for each receiving antenna. The content that is different from the content of the first embodiment is described below with reference to FIG. 10.

A scanned section in which scanning will be performed is set for the receiving antennas 3a to 3h themselves. A user sets a scanned section of each of the receiving antennas by using the operating unit 44. For example, a user disposes the receiving antennas on a subject that is displayed in the output unit 45 or the display device 6, in accordance with actual mounting positions. Then, the user sets a scanned section for each of the receiving antennas. Specifically, a plurality of scanned sections 32a is set for the receiving antenna 3a. Similarly, a plurality of scanned sections 32b is set for the receiving antenna 3b, a plurality of scanned sections 32c is set for the receiving antenna 3c, a plurality of scanned sections 32d is set for the receiving antenna 3d, a plurality of scanned sections 32e is set for the receiving antenna 3e, a plurality of scanned sections 32f is set for the receiving antenna 3f, and a plurality of scanned sections 32h is set for the receiving antenna 3h.

In the third embodiment, scanned sections have been set in advance for the receiving antennas, but in the fifth embodiment, a user arbitrarily sets scanned sections for the receiving antennas.

Mode switching processing according to the present fifth embodiment can be performed similarly to the flowchart of FIG. 6 described above.

In the fifth embodiment described above, switching is performed to the wide area mode or the narrow half-power angle mode on the basis of an index that has been calculated on the basis of a received signal, and a signal of an appropriate receiving antenna or a signal of a scanned section is received. According to the present fifth embodiment, a wireless signal can be reliably obtained.

In addition, in the present fifth embodiment, a user arbitrarily sets scanned sections, and therefore a position desired by the user can be reliably scanned.

Sixth Embodiment

Figure 11:
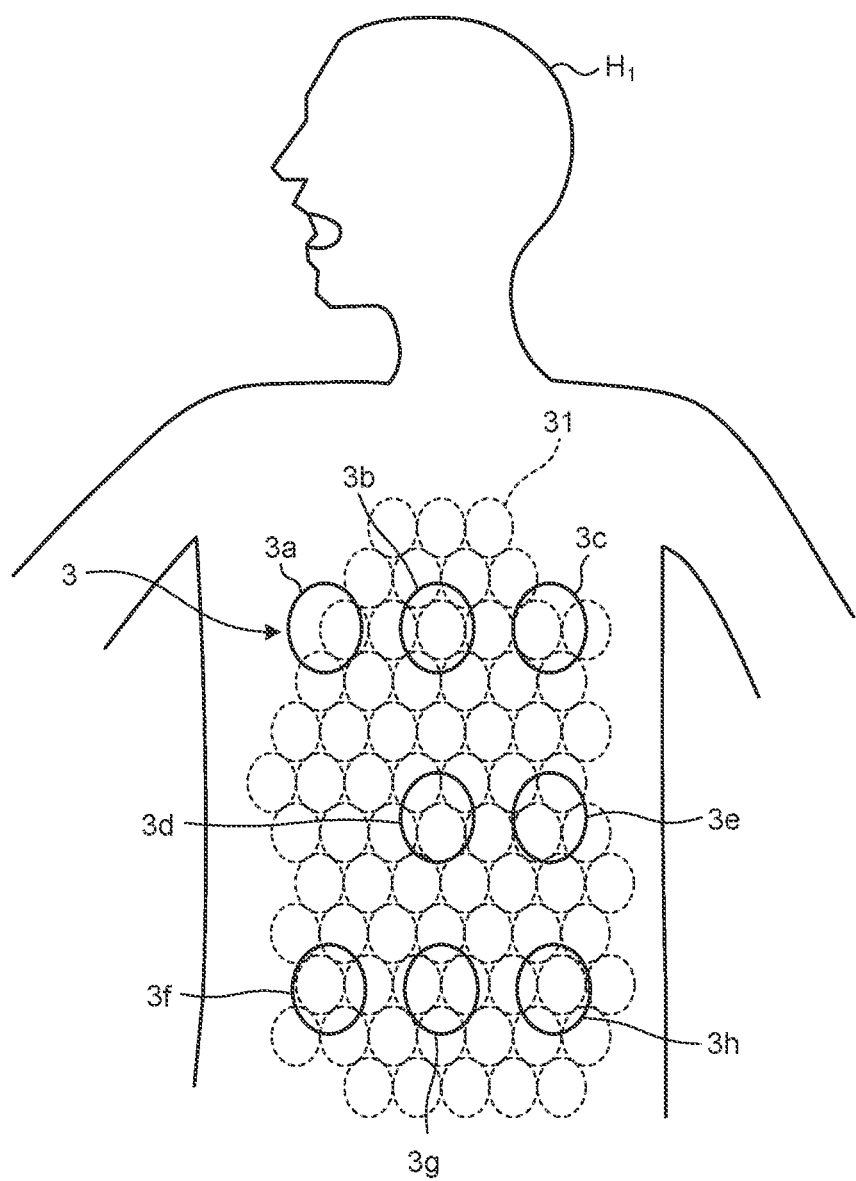
FIG. 11 is a diagram explaining a scanned section of a receiving antenna in a capsule endoscope system according to a sixth embodiment of the disclosure.

Next, a sixth embodiment of the disclosure is described. FIG. 11 is a diagram explaining a scanned section of a receiving antenna in a capsule endoscope system according to the sixth embodiment of the disclosure. A configuration of the capsule endoscope system according to the present sixth embodiment is similar to the configuration of the capsule endoscope system 1 according to the first embodiment. The sixth embodiment is different from the first embodiment in a scanned section that is set for each receiving antenna. The content that is different from the content of the first embodiment is described below with reference to FIG. 11.

In the present sixth embodiment, in a case where the capsule endoscope system 1 is used for a subject $H_1$ having a physique that is larger than a physique of the subject H described above, a certain number of scanned sections 31 that is greater than the number of scanned sections 31 that are set for the subject H are set. Scanned sections are allocated to each of the receiving antennas 3a to 3h, and in the case of the subject $H_1$, the number of scanned sections to be allocated to a single receiving antenna is greater than the number of scanned sections to be allocated in the case of the subject H.

Mode switching processing according to the present sixth embodiment can be performed similarly to the flowchart of FIG. 6 described above.

In the sixth embodiment described above, switching is performed to the wide area mode or the narrow half-power angle mode on the basis of an index that has been calculated on the basis of a received signal, and a signal of an appropriate receiving antenna or a signal of a scanned section is received. According to the present sixth embodiment, a wireless signal can be reliably obtained.

In addition, in the sixth embodiment described above, the number of scanned sections is increased or decreased according to the physique of a subject, and therefore scanned processing can be reliably performed regardless of the physique of the subject.

Seventh Embodiment

Figure 12:
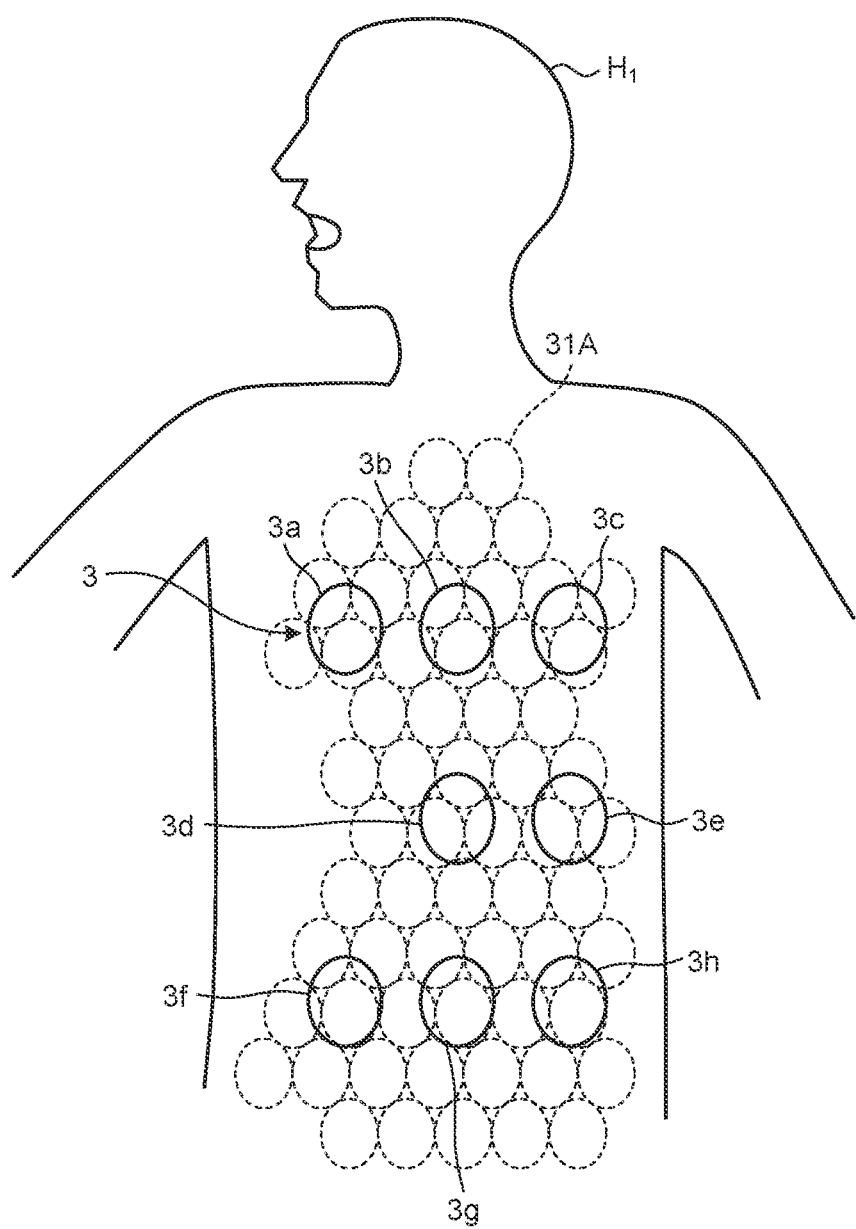
FIG. 12 is a diagram explaining a scanned section of a receiving antenna in a capsule endoscope system according to a seventh embodiment of the disclosure.

Next, a seventh embodiment of the disclosure is described. FIG. 12 is a diagram explaining a scanned section of a receiving antenna in a capsule endoscope system according to the seventh embodiment of the disclosure. A configuration of the capsule endoscope system according to the present seventh embodiment is similar to the configuration of the capsule endoscope system 1 according to the first embodiment. The seventh embodiment is different from the first embodiment in a scanned section that is set for each receiving antenna. The content that is different from the content of the first embodiment is described below with reference to FIG. 12.

In the present seventh embodiment, in a case where the capsule endoscope system 1 is used for the subject $H_1$ having a physique that is larger than a physique of the subject H described above, a scanned section 31A to be set for the subject H that has a size that is larger than a size of the scanned section 31 is set. By setting the scanned section 31A, a scanned range can also be set over the entirety of the subject $H_1$ having a large physique. The scanned section 31A is allocated to each of the receiving antennas 3a to 3h.

Mode switching processing according to the present seventh embodiment can be performed similarly to the flowchart of FIG. 6 described above.

In the seventh embodiment described above, switching is performed to the wide area mode or the narrow half-power angle mode on the basis of an index that has been calculated on the basis of a received signal, and a signal of an appropriate receiving antenna or a signal of a scanned section is received. According to the present seventh embodiment, a wireless signal can be reliably obtained.

In addition, in the seventh embodiment described above, a size of a scanned section is increased or decreased according to the physique of a subject, and therefore scanned processing can be reliably performed regardless of the physique of the subject.

Eighth Embodiment

Figure 13:
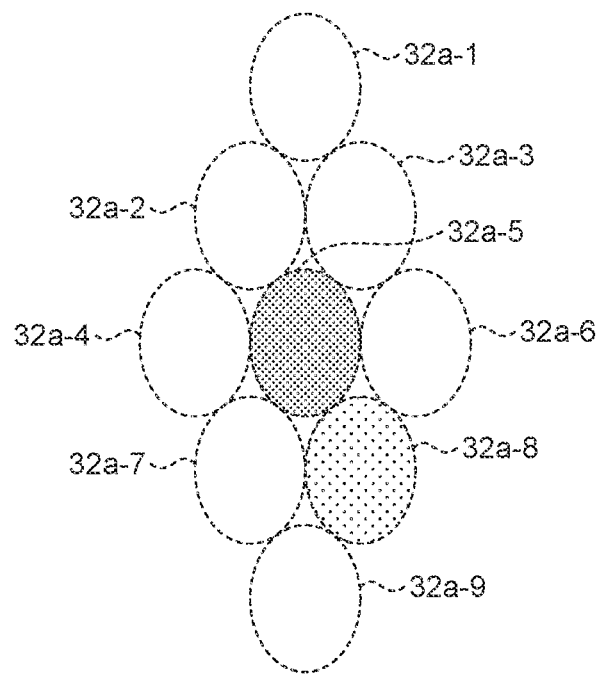
FIG. 13 is a diagram (no. 1) explaining mode switching processing at the time of obtaining image data that is performed by a capsule endoscope system according to an eighth embodiment of the disclosure.
Figure 14:
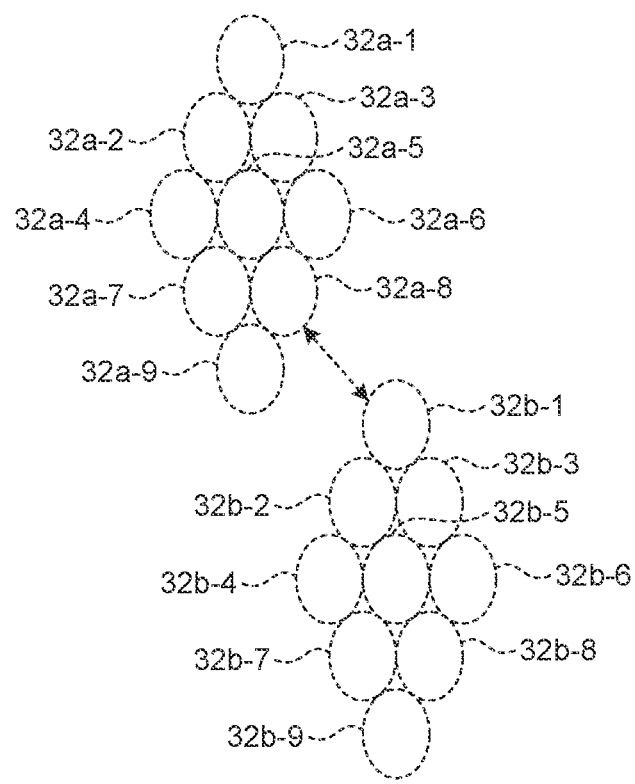
FIG. 14 is a diagram (no. 2) explaining mode switching processing at the time of obtaining image data that is performed by the capsule endoscope system according to the eighth embodiment of the disclosure.

Next, an eighth embodiment of the disclosure is described. FIGS. 13 and 14 are diagrams explaining mode switching processing at the time of obtaining image data that is performed by a capsule endoscope system according to the eighth embodiment of the disclosure. A configuration of the capsule endoscope system according to the present seventh embodiment is similar to the configuration of the capsule endoscope system 1 according to the first embodiment. The eighth embodiment is different from the first embodiment in a method for setting a scanning order of a scanned section. The content that is different from the content of the first embodiment is described below with reference to FIGS. 13 and 14.

In the present eighth embodiment, a scanning order of a scanned section is set by using an index that has been calculated a previous time. For example, it is assumed that in scanned sections 32a-1 to 32a-9 illustrated in FIG. 13, a previous result of calculating an index indicates that the scanned section 32a-5 has a highest index, and the scanned section 32a-8 has a second highest index. The index calculating unit 421 ranks the scanned sections on the basis of a magnitude of the index, and stores ranks as index information in the storage unit 47.

In Steps S107 and S108 of the flowchart illustrated in FIG. 6, the mode switching unit 423 refers to the storage unit 47, and obtains information relating to a previous index.

In a case where the same receiving antenna as a previous one has been selected

The mode switching unit 423 sets a scanning order on the basis of the ranks. In the example of FIG. 13, scanning is performed in the order of the scanned sections 32a-5, 32a-8, . . . . A third scanned section and sections that follow may be set in descending order of the index, or may be set on the basis of preset conditions (for example, in ascending order of a number).

In a case where a receiving antenna that is different from a previous one has been selected The mode switching unit 423 sets a scanning order on the basis of ranks of scanned sections of a previously selected receiving antenna. In a case where scanned sections 32b-1 to 302b-8 of a receiving antenna that has been selected this time and the scanned sections 32a-1 to 32a-9 of a receiving antenna that has been previously selected have the positional relationship illustrated in FIG. 14, the mode switching unit 423 performs setting in such a way that a scanned section that is closest to the receiving antenna that has been previously selected has a first scanning order. In the example illustrated in FIG. 14, setting is performed in such a way that the scanned section 32b-1 has a first scanning order. The mode switching unit 423 sets a second scanning order and scanning orders that follow in accordance with preset conditions.

Mode switching processing according to the present eighth embodiment can be performed similarly to the flowchart of FIG. 6 described above excluding Steps S107 and S108 described above.

In the eighth embodiment described above, switching is performed to the wide area mode or the narrow half-power angle mode on the basis of an index that has been calculated on the basis of a received signal, and a signal of an appropriate receiving antenna or a signal of a scanned section is received. According to the present eighth embodiment, a wireless signal can be reliably obtained.

In addition, in the eighth embodiment described above, a scanning order is set on the basis of a previously calculated index, and therefore efficient scanning processing can be performed. At this time, an index is calculated in every scanning, and in a case where an index that exceeds a reference value is obtained, scanning is terminated, and forming is performed. In this case, scanning processing is not performed in all of the scanned sections, and the time required in forming can be reduced.

Note that the present eighth embodiment can be applied to the first to seventh embodiments described above.

The preferred embodiments of the disclosure have been described above, and the disclosure is not to be only limited to the embodiments described above and variations. The disclosure is not limited to the embodiments described above and the variations, and can include various embodiments without departing from technical ideas described in the claims. In addition, configurations of the embodiments and the variations may be appropriately combined.

Note that in the first to eighth embodiments described above, an index that is used to select a receiving antenna and an index that is used to select a scanned section may be the same parameter, or may be parameters different from each other. In the first embodiment described above, an example where the same index (an RSSI) is used has been described, but the RSSI may be set as the index that is used to select the receiving antenna, and a counted value of a sync word may be set as the index that is used to select the scanned section.

In addition, in the first to eighth embodiments described above, an example where mode switching processing is performed by the receiving device 4 has been described, but a configuration in which the mode switching processing is performed by the processing apparatus 5 may be employed.

Further, in the first to eighth embodiments described above, description has been provided by using the capsule endoscope 2 as an example of a medical device, but this is not restrictive. For example, an implant medical device, a catheter, or a medical device that is introduced into a subject, obtains pH information, and outputs the pH information as a wireless signal may be employed. In addition, an endoscope of a type different from a capsule type, for example, a medical device that outputs, as a wireless signal, an image signal captured by an endoscope that performs wireless communication with a processing apparatus, may be employed.

Furthermore, an execution program for each processing performed by each constituent unit of the capsule endoscope 2, the receiving device 4, and the processing apparatus 5 of the capsule endoscope system 1 according to the present embodiments may be recorded in the form of a file of an installable format or an executable format in a computer-readable recording medium, such as a CD-ROM, a flexible disk (FD), a CD-R, or a DVD, and may be provided. Alternatively, the execution program may be stored on a computer that is connected to a network such as the Internet, and may be provided by downloading the execution program via the network. Moreover, the execution program may be provided or distributed via the network such as the Internet.

As described above, an antenna system, a capsule endoscope system, and an operation method of the antenna system according to the disclosure are useful in reliably obtaining a wireless signal.

The disclosure exhibits an effect in which a wireless signal can be reliably obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A processing apparatus comprising
a processor configured to:
compare a first index with a first reference value that has been determined for the first index, the first index indicating a receiving performance of a wireless final that has been received by a receiving antenna from a medical device configured to capture an image of an inside of a subject;
perform switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and
when the switching has been performed to the second mode, set a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

2. The processing apparatus according to claim 1, wherein the plurality of sections is set in accordance with the subject.

3. The processing apparatus according to claim 2, wherein the plurality of sections is set in positions where the receiving antenna is not mounted or in positions where presence of a gastrointestinal tract is expected in the subject.

4. The processing apparatus according to claim 1, wherein the plurality of sections is set in accordance with the receiving antenna.

5. The processing apparatus according to claim 1, wherein the processor is further configured to
rank each of the plurality of sections based on the second index, and
determine an order of setting the radiation direction toward the section based on ranking of the second index.

6. The processing apparatus according to claim 1, wherein the medical device includes a capsule endoscope.

7. The processing apparatus according to claim 1, wherein the first index and the second index are any of a received signal strength indicator of the wireless signal, a counted value of a sync word of the wireless signal, and a counted value of a bit error of the wireless signal.

8. A non-transitory computer-readable recording medium with an executable program stored thereon, the program causing a processing apparatus to execute:
comparing a first index with a first reference value that has been determined for the first index, the first index indicating a receiving performance of a wireless signal that has been received by a receiving antenna from a medical device configured to capture an image of an inside of a subject;
performing switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and
when the switching has been performed to the second mode, setting a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

9. The recording medium according to claim 8, wherein the plurality of sections is set in accordance with the subject.

10. The recording medium according to claim 9, wherein the plurality of sections is set in positions where the receiving antenna is not mounted or in positions where presence of a gastrointestinal tract is expected in the subject.

11. The recording medium according to claim 8, wherein the plurality of sections is set in accordance with the receiving antenna.

12. The recording medium according to claim 8, wherein the program further causes the processing apparatus to execute:
ranking each of the plurality of sections based on the second index; and
determining an order of setting the radiation direction toward the section based on the ranking of the second index.

13. The recording medium according to claim 8, wherein the first index and the second index are any of a received signal strength indicator of the wireless signal, a counted value of a sync word of the wireless signal, and a counted value of a bit error of the wireless signal.

14. An operation method comprising:
comparing a first index with a first reference value that has been determined for the first index, the first index indicating a receiving performance of a wireless signal that has been received by a receiving antenna from a medical device configured to capture an image of an inside of a subject;
performing switching to a first mode or a second mode based on a result of the comparing, the first mode causing a half-power angle of the receiving antenna to be set to a value that is greater than a predetermined threshold, the second mode causing the half-power angle of the receiving antenna to be set to be less than or equal to the predetermined threshold; and
when the switching has been performed to the second mode, setting a radiation direction of the receiving antenna toward a section in which a second index satisfies a condition relative to a second reference value that has been determined for the second index, from among a plurality of sections from which the receiving antenna receives the wireless signal, the second index indicating the receiving performance of the wireless signal that has been received.

15. The operation method according to claim 14, wherein the plurality of sections is set in accordance with the subject.

16. The operation method according to claim 15, wherein the plurality of sections is set in positions where the receiving antenna is not mounted or positions where presence of a gastrointestinal tract is expected in the subject.

17. The operation method according to claim 15, wherein the plurality of sections is set in accordance with the receiving antenna.

18. The operation method according to claim 14, further comprising ranking each of the plurality of sections based on the second index, and determining an order of setting the radiation direction toward the section based on the ranking of the second index.

19. The operation method according to claim 14, wherein the medical device includes a capsule endoscope.

\* \* \* \* \*